(12) United States Patent
Zandbergen

(10) Patent No.: US 9,922,797 B2
(45) Date of Patent: Mar. 20, 2018

(54) MICROREACTOR FOR USE IN MICROSCOPY

(71) Applicant: Technische Universiteit Delft, Delft (NL)

(72) Inventor: Hendrik Willem Zandbergen, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 0 days.

(21) Appl. No.: 15/582,073

(22) Filed: Apr. 28, 2017

(65) Prior Publication Data

US 2017/0236685 A1    Aug. 17, 2017

Related U.S. Application Data

(63) Continuation of application No. PCT/NL2015/050758, filed on Oct. 29, 2015.

(30) Foreign Application Priority Data

Oct. 29, 2014    (NL) ..................... 2013706

(51) Int. Cl.
*H01J 37/20* (2006.01)
*H01J 37/26* (2006.01)
*B01J 19/00* (2006.01)

(52) U.S. Cl.
CPC ........... *H01J 37/20* (2013.01); *B01J 19/0093* (2013.01); *H01J 37/26* (2013.01);
(Continued)

(58) Field of Classification Search
CPC .... H01J 37/20; H01J 37/26; H01J 2237/2003; B01J 19/0093; B01J 2219/00783;
(Continued)

(56) References Cited

U.S. PATENT DOCUMENTS

| 8,837,754 B2 | 9/2014 | Formosa et al. |
| 2011/0006208 A1* | 1/2011 | Freitag ............... G01N 23/2251 250/307 |
| 2012/0298883 A1* | 11/2012 | Grogan .................. H01J 37/20 250/440.11 |

FOREIGN PATENT DOCUMENTS

| DK | EP 2626884 A1 * | 8/2013 | ......... G01N 23/2251 |
| EP | 2626884 | 8/2013 | |

(Continued)

OTHER PUBLICATIONS

Oh, et al., "A review of microvalves", J. Micromech. Microeng., vol. 16, No. 5, 2006, R13-R39.
(Continued)

*Primary Examiner* — David E Smith
(74) *Attorney, Agent, or Firm* — Peacock Law P.C.; Jeffrey D. Myers; Janeen Vilven

(57) ABSTRACT

An improved microreactor for use in microscopy, use of said microreactor, and a microscope comprising said reactor. The present invention is in the field of microscopy, specifically in the field of electron and focused ion beam microscopy (EM and FIB), and in particular Transmission Electron Microscopy (TEM). However its application is extendable in principle to any field of microscopy, especially wherein characteristics of a (solid) specimen (or sample) are studied in detail, such as during a reaction.

15 Claims, 2 Drawing Sheets

(52) U.S. Cl.
CPC ............... *B01J 2219/0093* (2013.01); *B01J 2219/00783* (2013.01); *B01J 2219/00853* (2013.01); *B01J 2219/00862* (2013.01); *B01J 2219/00873* (2013.01); *H01J 2237/2003* (2013.01)

(58) Field of Classification Search
CPC .... B01J 2219/00853; B01J 2219/00862; B01J 2219/00873; B01J 2219/0093
See application file for complete search history.

(56) References Cited

FOREIGN PATENT DOCUMENTS

| NL | WO 2011019276 A1 * | 2/2011 | ........ B01L 3/502707 |
|---|---|---|---|
| WO | 2011/019276 | 2/2011 | |
| WO | 2016/068710 | 5/2016 | |

OTHER PUBLICATIONS

Xin, et al., "In Situ TEM Study of Catalytic Nanoparticle Reactions in Atmospheric Pressure Gas Environment", Microscopy and Microanalysis, vol. 19, No. 6, 2013, 1558-15868.

* cited by examiner

MICROREACTOR FOR USE IN MICROSCOPY

CROSS-REFERENCE TO RELATED APPLICATIONS

This application is a continuation application of Patent Cooperation Treaty Application No. PCT/NL2015/050758, entitled "Improved Micro-reactor for use in microscopy", to Technische Universiteit Delft, filed on Oct. 29, 2015, which claims priority to Netherlands Patent Application No. 2013706, filed Oct. 29, 2014, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

FIELD OF THE INVENTION (TECHNICAL FIELD)

The present invention is in the field of an improved small reactor for use in microscopy, use of said small reactor, and a microscope comprising said reactor.

BACKGROUND OF THE INVENTION

The present invention is in the field of microscopy, specifically in the field of electron beam microscopy (EM) and Scanning Transmission X-ray Microscope (STXM), and in particular Transmission Electron Microscopy (TEM). However its application is extendable in principle to any field of microscopy, especially wherein characteristics of a (solid) specimen (or sample) are studied in detail, such as during a reaction.

Microscopy is a technique used particularly in semiconductor and materials science fields as well as for biological samples for site-specific analysis, and optionally deposition, and ablation of materials. Also it is widely used in life sciences to obtain information. The resolution domain is typically from 0.1 nm to 1 µm. In microscopy typically a source is used to obtain an image. The source may be a source of light, electrons, and ions. Further scanning techniques have been developed using e.g. atomic force (AFM) and scanning tunnelling. Under optimal conditions a modern microscope can image a sample with a resolution typically in the order of a few tenths of nanometres for a TEM, a nanometre for a FIB and Scanning (S)EM, and a few hundred nanometres for an optical microscope.

The present invention relates to micro-reactors and nano-reactors, i.e. having a reaction volume in the order of $10^{-9}$ m$^3$. Reference throughout the description to a reactor refers to said micro-reactors and nano-reactors. Typically a to be observed sample is positioned in a reactor; the sample is typically attached to a second wall, the bottom, and above the sample between the bottom and first wall, the top, a (virtual) column is present through which an observation is made.

A problem with prior art microreactors, especially when used in an environment having a substantially different pressure from the inside of the reactor, is that the thin observation windows and/or reactor wall (or membrane) tend to bulge outwards or inwards, depending on the environmental pressure. Bulging can be in the order of several µm-100 µm, thereby extending/shrinking a (virtual) column above/beneath a sample. Especially the outward bulging can be much larger than a height of the original column. Such is especially the case for gas and liquid nanoreactors for in-situ transmission electron microscopy experiments. Such nanoreactors typically consist of two thin membranes, which allows one to enclose a gas or liquid in between the membranes and still maintain a very good vacuum in the electron microscope. One of the big problems in the use of gas and liquid nanoreactors in an electron microscope is that the electron transparent membranes are bulging outwards due to the pressure difference between the microscope (ultra-high vacuum) and the inside of the nanoreactor (for instance 1 bar). Whereas one prefers gas columns of less than 5 µm and liquid columns of less than 0.5 µm, the bulging can lead in to column lengths of 20 µm and more.

WO2011019276 (A1) recites a method of manufacturing a micro unit for use in a microscope. The method comprises the step of providing a planar substrate supporting structure and creating a chamber in the supporting structure for receiving a fluid containing a chemically reacting substance to be inspected. Further, the method comprises the step of coating an inner surface of the chamber with a thin layer. The method also comprises the step of locally removing material from the exterior of the supporting structure until the thin layer is reached for forming a window segment that is at least partially transparent to a beam of radiation generated by the microscope. It has been found that such a micro unit allows one to prevent bulging of the membranes away from each other. However, the micro unit is found to be impractical; the sample has to be loaded by use of a liquid suspension of particles of interest and therefore there is no control on a final position of the sample and as a result the sample is typically positioned where it can not be observed; and the sample is not positioned at a desired location where it can be manipulated properly, such as by heating, by performing a reaction, etc.; and the manipulation of the sample cannot be controlled properly, such because heating is non-uniform. With some materials this approach may be useful, but for many others it is required to put a sample into the nanoreactor at a very special location. Thus this method is not very useful for most applications.

EP 2 626 884 A1 recites a method for fabricating a microfluidic chip for transmission electron microscopy, which has a monolithic body with a front side and a back side. The monolithic body comprises an opening on the back side extending in a vertical direction from the back side to a membrane on the front side, the membrane being supported at edges of the opening and extending across the opening, and a microfluidic channel comprising on top of the membrane a sample chamber with a top window towards the front side and a bottom window towards the back side, the top and bottom windows being aligned with each other so as to allow for observation of a sample volume between the top and bottom windows inside the sample chamber in a transmission configuration along an axial direction, wherein the dimension of the membrane in at least one horizontal direction exceeds the dimension of the sample chamber in that direction. Clearly the sample itself must relate to a liquid or gas, which can only be introduced into the chamber by microfluidic action of the chip. Certain drawbacks are still present in this device, such as not having control on the parallel positions of the membranes. This document inherently relates to a monolithic body with a reactor having internal pillars for controlling bulging and considers c.q. teaches no other options for controlling said bulging. Also this document shows the feasibility of using a piezoelectric layer for a totally different purpose, i.e. a strain gauge for determining the deformation of the window, without mentioning a further use thereof. It is known however that semiconductor strain gauges are fragile, i.e. break easily, and therefore have limited use. If a strain gauge foil would be intended, than this type of foil is not considered suited for nanoreactors.

Oh et al. in Journal of micromechanics and microengineering in March 2006, p 13-30 gives a brief overview of micro valves, including a piezoelectric actuated microvalve. Therein microvalves were employed for gas flow regulations, i.e. pumping action.

U.S. Pat. No. 8,837,754 B2 recites a method for fabricating a MEMS transducer, which has a micromechanical sensing structure for sensing and a package. The package is provided with a substrate, carrying first electrical-connection elements, and with a lid, coupled to the substrate to define an internal cavity, in which the micromechanical sensing structure is housed. The lid is formed by a cap layer having a first surface and a second surface, set opposite to one another, the first surface defining an external face of the package and the second surface facing the substrate inside the package; and a wall structure, set between the cap layer and the substrate, and having a coupling face coupled to the substrate. At least a first electrical component is coupled to the second surface of the cap layer, inside the package, and the coupling face of the wall structure carries second electrical-connection elements, electrically connected to the first electrical component and to the first electrical-connection elements. However, using microvalves and MEMS transducers for controlling the bulging is not mentioned in these latter two documents. Even further, the MEMS and strain gauges are only used to measure and there is no mention of any other use, let alone control.

The present invention therefore relates to an improved reactor assembly, and use thereof, which solve one or more of the above problems and drawbacks of the prior art, providing reliable results, without jeopardizing functionality and advantages.

BRIEF SUMMARY OF THE INVENTION

The present invention relates to a reactor assembly according to claim 1, and a use of said reactor assembly according to claim 14. The present system is especially suited for gas and liquid nanoreactors for in-situ (transmission) electron microscopy experiments. The present assembly may relate to two nanoreactor halves, in order to make it possible to put a sample on one half of the reactor and thereafter put the nanoreactor together. This method of sample loading is incompatible with the presence of pillars connecting two opposite membranes. In other words, the present reactor allows for placement or likewise introduction of a (most often solid) sample into the reactor, i.e. parts of the present reactor may be taken apart, the sample may be introduced, and the reactor may be assembled again, hence a reactor assembly of which at least one part is detachable.

The present reactor comprises reactor walls. Two of these walls are located opposite of one and another, or put in other words are mutually facing one and another, and are typically substantially parallel to one and another. The walls are typically made of a flexible material allowing some deformation, such as bending, e.g. allowing a bulging with a vertical displacement at a given location, the displacement being relative to an average position, of up to 0.2 µm/1 µm length, typically of 0.05 µm/1 µm length.

At least one of the walls comprises at least one window, wherein the at least one window which is transparent for electrons. As such the window allows inspection of an underlying sample or the like. In case of transmission microscopy two windows are provided located opposite of one and another, one in a first wall, and one in a second wall. The wall, sometimes referred to as membrane, may be of such nature that it effectively is a window, such as in the case of STXM.

The present reactor is characterized in that it has as a controller of parallel positions, or likewise distance, of opposite walls, which controller comprises at least one first capacitive plate (51) and at least one second capacitive plate (52) arranged to cooperate with the at least first capacitive plate. In general it is noted that the objective of controlling is clearly totally different from sensing. The first plate is located at the first side of the nanoreactor or is attached to said first side. The second plate is located at the second side of the nanoreactor or is attached to said second side. The capacitive plates (51,52) are separated from the reactor by a dielectric material, such as a dielectric layer of silicon nitride; hence the present capacitive plates are not in contact with contents of the reactor, such as liquids and gases. The capacitive plates may be inactive e.g. when not in use, i.e. having no charge, or may be active, having a charge, the charge being provided by e.g. a voltage source 71. In order to compensate bulging due to under-pressure of an outside of the reactor the first and second side are attracted to one and another, such as by providing a charge on the first and second of opposite nature (+ and −). In order to potentially compensate inward curving due to under-pressure of an inside of the reactor the first and second side are repelled, e.g. by providing a charge on the first and second side of similar nature (+ and +, or − and −).

The first and second capacitive plates may have a form which is suitable for the present reactor assembly, wherein each form is individually selected. Each plate may be integrated in the respective side, may be attached to said side, may be the same as said side, and combinations thereof.

For the capacitive plates a material is selected which is suitable for the purpose, namely storing electric charge. Typically the present capacitive plates a surface area thereof is sufficient to store a relatively small amount of charge. A capacitance of the capacitive plates used is typically 0.01-10 pF. The material of the capacitive plates may be selected from conducting materials, preferably cleanroom compatible materials and manufacturing process compatible materials, such as molybdenum, aluminium, and semi-conducting material, such as (doped) silicon. As the walls, the capacitive plates are typically made of a flexible material allowing some deformation, such as bending and displacement.

The capacitive plates may serve a further function; as such a selection of appropriate material may be adapted in view thereof. For instance, use is made of attraction by a plate of e.g. a charged gas/liquid or a molecule therein. The electric field will affect charged species, such as causing them to travel parallel or anti-parallel to the field. Such may influence reactions in the reactor, such as between a sample and a liquid.

By using capacitive plates or the like a distance between the two walls can be fixed, changed, controlled, and combinations thereof, thereby providing e.g. a virtual inspection volume above a sample that remains as constant as possible. In preferred exemplary embodiments further details are given providing even better control of e.g. the distance.

In an example the present reactor may be considered as a method of realising exactly the intended length of a gas column or liquid column in in-situ electron microscopy experiments using a nanoreactor.

Thereby the present invention provides a solution to one or more of the above mentioned problems and drawbacks.

Advantages of the present description are detailed throughout the description.

DETAILED DESCRIPTION OF THE INVENTION

The present invention relates in a first aspect to a reactor assembly according to claim 1.

In an example of the present reactor assembly the at least one first plate is fully integrated in the first side. The at least one first plate may be incorporated in the first side, may form the first side, may be part of the first side, and combinations thereof. The material of the first side is selected such that it is (also) suited for an intended purpose of the reactor, e.g. such that it can withstand (aggressive) chemicals used in the reactor.

In an example of the present reactor assembly the at least one second plate is fully integrated in the second side.

Similar considerations as above for the first side are applicable to the second side.

In an example of the present reactor assembly the reactor comprises at least one means (71) for providing an electric field to the capacitive plates. An example thereof is an electric potential generator of 0.5-100 V (DC), such as 1-10 V. It has been found that under given circumstances (a reactor with a width of 600 µm and a height of 20 µm) a relative small electrical potential of e.g. 7 V is sufficient to attract the two sides to one and another, and e.g. thus to withstand bulging. An attractive force would depend on a surface area A of a capacitor plate, a distance L between the plates, and a charge on the plates. It is noted that once the plates are attracted and close to one and another (e.g. clamped) a much smaller potential (electric field) may be applied, such as less than 1 V.

In an example of the present reactor assembly the reactor has a volume of less than $10^9$ µm$^3$ that is a relatively small reactor. Typical dimensions are a length of 100-1000 µm, a width of 100-1000 µm, and a height typically depending on a physical nature of reaction chemicals used. For instance, the sides are located at a distance (d) of 0.1-5 µm for a reactor comprising a liquid, and at a distance of 0.1-100 µm for a reactor comprising a gas. A relatively large width and length of the nanoreactor are preferred to allow bulging by the capacitor plates over a relatively large distance, such that the starting distance is less critical. In view of reaction conditions and reactor behaviour the reactor is preferably large enough to ensure e.g. proper heat transfer; such a relatively larger reactor would suffer more from bulging (0.5-5% (Δheight/width) outward/inward bending); a smaller reactor would have less bulging (percentage wise) but would have unfavourable heat transfer characteristics, hence relatively more drift.

In an example of the present reactor assembly the first side and second side comprise at least one membrane (21), the at least one membranes being located opposite of one and another. The present membranes for use in an electron microscope contain areas, such as windows, that are largely transparent for electrons, such as more than 95% transparent, and preferably being amorphous. They are typically relatively thin, such as 10-1000 nm, e.g. 20-100 nm. If used for inspecting chemical reactions, the membranes are preferably also chemically inert to the reactants and optional reaction products. A suitable material is for instance a nitride, such as SiN, and AlN.

A disadvantage with using only two capacitive plates is that the plates exert a relatively strong force upon one and another, thereby forcing the two sides into (physical) contact with one and another. For some applications such a contact is acceptable, for others it is not. In order to prevent contact and in order to maintain the two sides at a required distance the first side and/or second side comprise at least one spacer (81) for maintaining a minimum distance between the first and second side. It is preferred to use non-conducting or semi-conducting materials for the at least one spacer, typically having a dielectric constant ($\in_r$) being large enough, such as $\in_r$>2. A thickness of the spacers is in the order of the column length as mentioned above, e.g. a height of 0.1-5 µm for a reactor comprising a liquid, and at a height of 0.1-1000 µm for a reactor comprising a gas. The spacer may also be formed of a suitable material, and coated with a (thin) layer of electrically insulating material. It is preferred to use a spacer having similar or the same material as e.g. used for the present window or membrane; in other words to use a material that fits in a manufacturing process of the present assembly. The spacer may form an integral part of a side, may be formed by an etch process, may be formed by a deposition process, may be in the form of an adherent layer or foil, and combinations thereof. The spacer may be provided in part of a viewing window, may be provided aside of the viewing window, and combinations thereof, preferably aside of the viewing window. In a further example the spacer (or spacer element) can be inserted in between capacitor plates. One part is formed thereby comprising the spacer as well as at least one sample. The present spacer can not be connected or attached to (both of) two opposite sides as the present assembly would then not allow placement or introduction of a sample into the reactor; the present spacer may however be in contact with two opposite sides when a distance between these two opposite sides becomes small enough as a consequence of (internally directed) deformation of at least one of the two sides.

In an example of the present reactor assembly it further comprises at least one second capacitor for controlling a distance between the first and second side, and at least one second means for providing an electric field to the at least one second capacitor, wherein the electric field of the second capacitor and of the capacitive plates may be of opposite nature, when applied, i.e. an attracting/repelling force of the plates is potentially countered/supported by a repelling/attracting force of the second capacitor, respectively. In addition to the at least one spacer, or as an alternative, the second capacitor may be provided. The spacer may be considered to provide a passive control of the distance of the two sides (safeguarding a minimum distance), whereas the second capacitor may provide active control in that by varying and controlling an electrical field thereof a counter force for the first capacitor may be provided, which counter force and force of the first capacitor can be controlled precisely. The forces of the capacitors, optional forces of temperature change, and forces of pressure difference (between an inside and outside (microscope) of the reactor) may be controlled, may be balanced, may be limited, may be changed, may be regulated, and combinations thereof. The present second capacitor is preferably in a three dimensional form, such as an extension element and a receiving element, respectively, having an opening substantially in a similar form as the extension element, wherein its form provides for a better control of distance when exerting an electrical field. The extension element may be in the form of a pin, the pin being circular, rectangular, hexagonal, multigonal, ellipsoid, and combinations thereof. In an example the at least one first and at least one second capacitive plates are one and the same as the at least one second capacitor.

In an example of the present reactor assembly it further comprises a controller for controlling a distance between the first and second side. The controller is preferably an electrical controller. The controller is preferably provided with a feedback loop.

In an example of the present reactor assembly it may further comprise various other elements, such at least one heater. Examples of heaters are a MEMS-heater, and a capacitive heater, and combinations thereof. An advantage with a MEMS heater is that heating (of a sample) can be obtained with a very small power (mW). As such in-situ experiments can be performed at elevated temperatures.

In an example the present holder comprises a sample (micro)heat provider 23. It has been found experimentally that it is preferred to provide as little heat as possible to the sample to reach or maintain a given temperature and thus it is preferred to use a heater on which the specimen is located, whereby the heat transfer from the heater/specimen to the holder is as small as possible. This can be realised with a MEMS device with a microheater in a thin membrane for instance 0.2 micron thick SiN. The heater (MEMS device) preferably comprises a temperature sensor and a heater, in order to rapidly decrease or increase the temperature in a controlled and reproducible manner.

In an example the reactor assembly one or more of the capacitor plates comprises two sections with an outer section for main clamping and an inner section that can be activated independently, whereby this inner section is used for realising relatively small changes in the local distance between the two walls to allow switching between the minimum column length determined by the spacers and a maximum column length determine by the opposite bulging forces. This allows in the case of diffusion limitations in the narrow space between the two walls a normal reaction when the column is maximal and (TEM) imaging at intervals where the column is short. The inner section may be located in a more central part of the assembly, and the outer section in a more peripheral part of the assembly. In a less preferred alternative the inner section may be located closer to the reactor of the assembly, and the outer section further away from the reactor, e.g. in a stacked geometry.

In a second aspect the present invention relates to a use of the present reactor according to claim 14.

In an example the reactor assembly is used to control bulging. The bulging may be limited to acceptable levels or may be cancelled by the use of the present capacitive plates.

In an example the reactor is used to fix a sample. In such a case a sample is placed in between the present capacitive plates, an electrical field is applied in order to contact the two plates, thereby fixing the sample. Such solves problems such as that often samples when inserted in a microscope loose contact with a support thereof, such as due to a temperature increase, and that samples have a poor electrical/thermal contact with e.g. a MEMS-heater.

In an example the reactor assembly is used to close a reaction chamber. Such provides the option of entering a samples and/or reactants into the chamber, mounting a reactor wall on top of the chamber, and securely closing the chamber by applying an electrical field. Likewise it may be used to close a channel.

In an example the reactor assembly is used to provide a pump function. By changing an electrical field between the plates a distance between the plates may be varied, and as a consequence locally a volume is increased or decreased. The change of volume causes reactants to flow and e.g. refresh a volume/area around the sample.

In an example the reactor assembly is used to provide pre-bending of a first and/or second wall. Such is especially relevant if a reactor temperature is increased or decreased; the change will cause bending of the reactor walls. By providing an initial bending (pre-bending) of a reaction wall, during a temperature change the bending can be relaxed, and the relaxation substantially compensates the bending due to the temperature change.

In an example the reactor assembly is used to apply a pressure. By forcing the two plates together, or by reducing a force and thereby allowing the plates to separate relative to one and another, a pressure change can be established. Hence during a reaction a pressure can (temporarily) be increased or reduced, or both, within given boundary conditions.

In an example the reactor assembly is used to maintain a pressure. For instance at a start of an experiment (outside a microscope) a pressure may be applied to the reactor. This pressure can be maintained by using the attractive force of the present plates. As such reaction at increased (or reduced) pressure can be performed.

In an example the reactor assembly is used to remove or replace a gas bubble in a liquid. Such a gas bubble may be captured in the reactor, e.g. upon closure thereof, may have been formed by reaction of the electron beam with the liquid, or may have been formed during reaction, etc. If the gas bubble is "in the way", e.g. in a viewing window, it may be removed or replaced by exerting or limiting a force on the present plates.

In an example the reactor assembly is used for removing unwanted charged particles. As such reaction conditions are further optimised.

In an example the reactor assembly is used for introducing wanted charged particles. As such reaction conditions are further optimised.

In an example the reactor assembly is used to reduce the liquid column for TEM inspection and allowing a larger liquid column for further reaction.

The above examples of use indicate that a wide variety of tools now has become available to manipulate reaction conditions.

In a third aspect the present invention relates to a microscope selected from an electron microscope, an ion microscope, an atomic force microscope, and an optical microscope, such as a TEM, a SEM, a transmission mode SEM, an STM, an STXM microscope, comprising a reactor assembly according to the invention.

In an example the present microscope comprises one or more of a control means selected from a controller, an ampere meter, a voltage meter, a heating means, a radiation source, a means for receiving the holder, an image forming device, and a cooler.

In an example the microscope comprises an electron microscope, such as a TEM and SEM, and an optical microscope integrated therein. That is both techniques can be used to analyse a sample in the present holder.

It is noted that the term "substantial" is intended to indicate that within a given accuracy, such as measurement, manufacturing, etc. elements are e.g. in line, etc.

The one or more of the above examples and embodiments may be combined, falling within the scope of the invention.

EXAMPLES

The invention is further detailed by the accompanying figures, which are exemplary and explanatory of nature and are not limiting the scope of the invention. To the person skilled in the art it may be clear that many variants, being obvious or not, may be conceivable falling within the scope of protection, defined by the present claims.

SUMMARY OF FIGURES

The invention although described in detailed explanatory context may be best understood in conjunction with the accompanying figures.

DETAILED DESCRIPTION OF THE FIGURES

Figure 1:
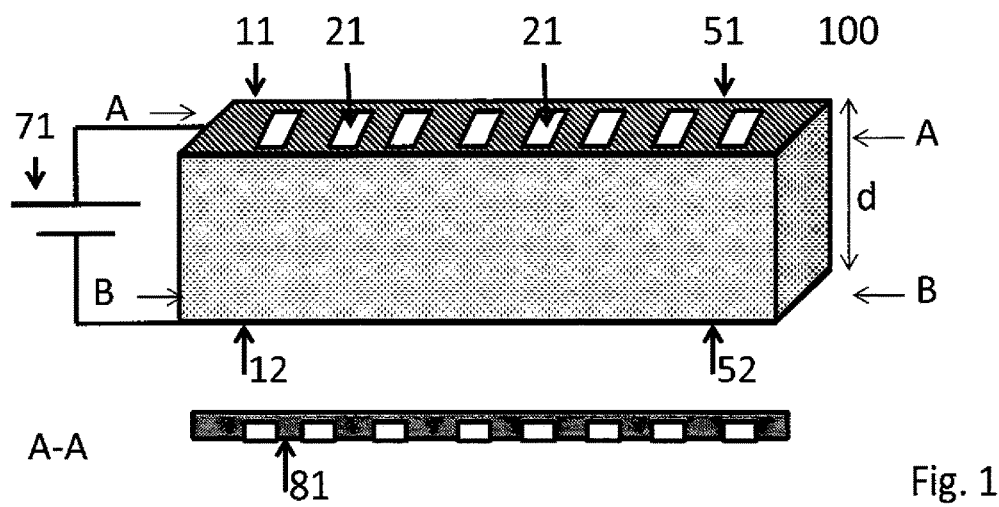
FIGS. 1-14 show various reactor assemblies which have (at least to some extent) been described throughout the description.

List of Elements:
11: First reactor wall
12: Second reactor wall
21: window c.q. membrane
22: column height
41: sample
51: capacitive plate
52: capacitive plate
53: dielectric layer
54: dielectric layer
56: first conductor second capacitor
57: second conductor second capacitor
61: heater
71: Voltage source
81a,b: spacer
91: outside section
92: inside section
A-A: Cross section
B-B: Cross section
100: reactor assembly
d: distance between first and second reactor wall at a given location FIG. 1 shows a reactor assembly 100. Therein two opposing walls 11 and 12 are shown, being at a (constant) distance d. Also various windows 21 for viewing are shown. The walls comprise at least one capacitive plate 51,52. A voltage 71 is applied. The cross-section A-A shows recesses resembling the windows and optional spacers 81.

Figure 2:
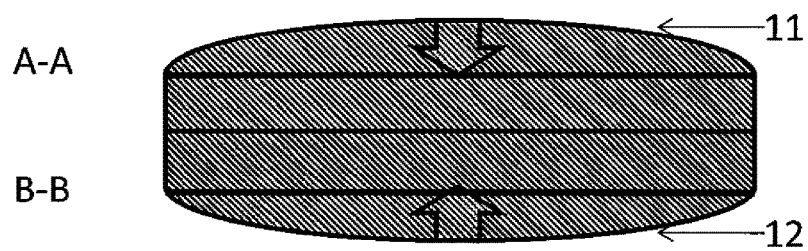

FIG. 2 shows a cross section indicating bulging of the first 11 and second 12 reactor wall.

Figures 3, 4:
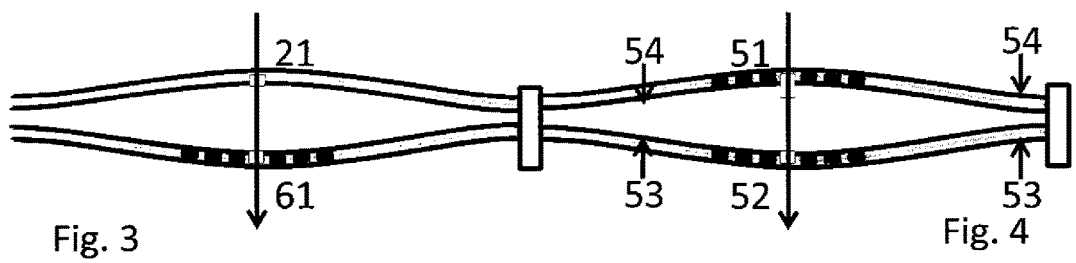

FIG. 3 shows a cross section of a prior art device. The arrow indicates a viewing direction. Further heating elements 61 are shown. Typically, a pressure inside the reactor is about 100 kPa (1 bar) and close to 0 kPa (0 bar) outside. The temperature of the device is not reviewed here. As a consequence of the pressure difference, significant bulging occurs.

FIG. 4 shows a cross section of a present device. The arrow indicates a viewing direction. Further capacitive elements 51,52 are shown. Also dielectric layers 53,54 are shown. In addition to these dielectric layers being present at an inside of the assembly, these layers may also be present at an outside of the assembly. Further conditions are the same as for FIG. 3. A temperature may be room temperature (about 20° C.). No electrical field is applied.

Figures 5, 6:
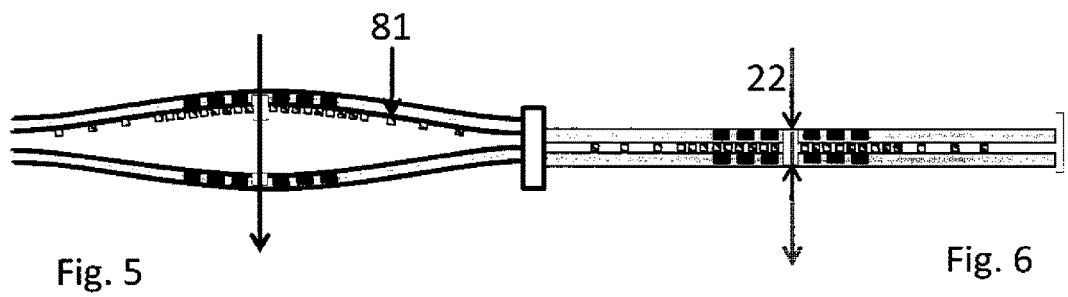

FIG. 5 shows the device of FIG. 4, further comprising spacers 81. The device is in a "bulged" situation. Further conditions are the same as for FIG. 4.

FIG. 6 shows the device of FIG. 5, in a situation wherein an electrical field is applied, the two walls are attracted to one and another, and the spacers prevent full contact between the two walls. A voltage difference of 7V is applied. Further conditions are the same as for FIG. 5. In the middle part of the figure also the (virtual) column height 22 is indicated.

Figures 7, 8:
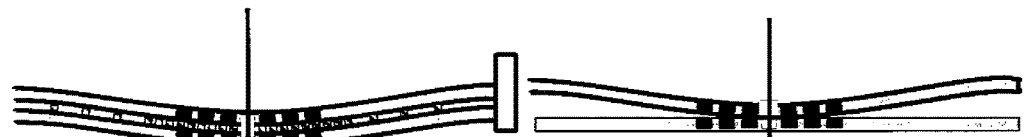

FIG. 7 shows the device of FIG. 6, in a situation wherein a temperature of 400° C. is applied. Despite the electrical field the reactor curves due to the temperature increase.

FIG. 8 shows the device of FIG. 6, in a situation wherein the reactor assembly is used to close a hole or channel. The hole or channel may comprise a (reaction) liquid or gas. Preferably a surface hydrophilicity is tuned and in order to obtain a good closure (especially for a gas) connecting surfaces adhere well.

Figures 9, 10:
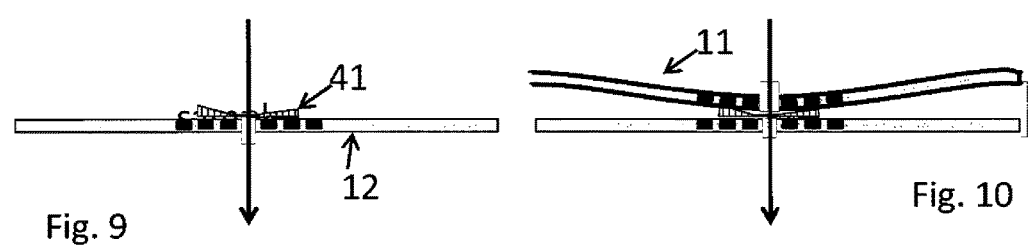

FIG. 9 shows a fixing of a sample 41 to a second wall 12.

FIG. 10 shows in addition to FIG. 9 a first wall 11. The reactor assembly now fixes the sample 41.

Figures 11, 12:
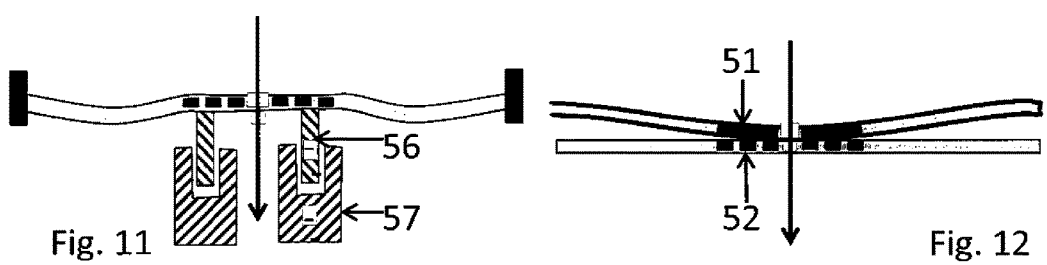

FIG. 11 shows a second capacitor having a first conductor 56 and a second conductor 57. In the example the first and second conductor have a similar charge and as a consequence potentially repel one and another. The repelling force may be used to control the distance d between the first and second wall. In the example the first conductor is in the form of an extension element, whereas the second conductor 57 has an opening for "receiving" the extension element.

FIG. 12 shows capacitor plates 51 and 52 having different shapes, forms, size, etc. Such may be in particular suitable for generating a wave, for pumping function, and for gas bubble removal.

Figure 13:
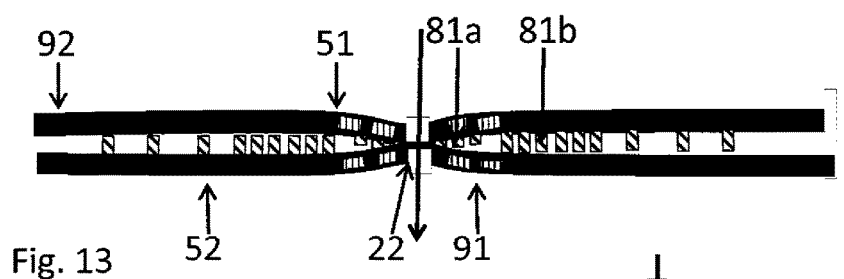

In addition to e.g. FIG. 12 in FIG. 13 spacers 81a,81b may have different sizes and shapes and additionally may be made of different materials. Spacers are typically provided on one side or on two opposite sides, and are typically not attached to both sides. The height of the spacers is typically less or at the most equal (50-100%) to a distance of two opposite walls in an "inactive" status. The device may have a 100 kPa pressure inside and a close to 0 kPa pressure outside. A voltage difference at an outside section 92 may be different from a voltage difference at an inside section 91, e.g. 5 V and 15 V respectively (at 20° C.). As such also a local variation in height of the column 22 may be obtained, by a second capacitive plate set (of which one voltage could be actually the same as that of the first capacitive pair). In an example hereof the black (peripheral) and dashed (central) blocks are two sets of capacitive plates. The central capacitive blocks are activated.

Figure 14:
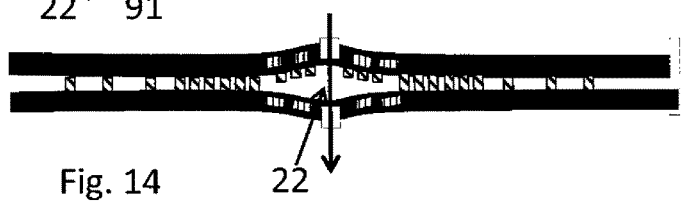

FIG. 14 shows the assembly of FIG. 13. In this case the central capacitive blocks are not activated and the reactor bulges outward. Playing around with the activation of the central capacitor has as advantage that in the situation where the capacitor is activated a higher resolution may be obtained, and in the case where the capacitor is not activated flow around a sample may be established or improved.

What is claimed is:

1. A nano- or micro-reactor assembly for use in an electron microscope comprising a reactor allowing placement of a sample into the reactor, the reactor comprising:

reactor walls, at least one wall being on a first side opposite of a second side, wherein the walls are flexible, and wherein at least one side comprises at least one window, and wherein the at least one window which is transparent for electrons, at least one first capacitive plate and at least one second capacitive plate arranged to cooperate with the at least one first capacitive plate for controlling parallel positions of the first and second side, wherein the at least one first plate is located at the first side of the nanoreactor or is attached to said first side, wherein the at least one second plate is located at the second side of the nanoreactor or is attached to said second side, and wherein the capacitive plates are separated from the reactor interior by a dielectric material, and at least one means for providing an electric field to the capacitive plates.

2. The reactor assembly according to claim 1, wherein the at least one first plate and/or the at least one second plate comprise at least two sections.

3. The reactor assembly according to claim 2 wherein the at least two sections comprise an inner section and an outer section.

4. The reactor assembly according to claim 1, wherein the inner and outer active sections can be activated independently, preferably wherein the inner section can be activated for realizing small changes in local distance between the two reactor walls.

5. The reactor assembly according to claim 1, wherein the at least one first plate is fully integrated in the first side.

6. The reactor assembly according to according to claim 1, wherein the at least one second plate is fully integrated in the second side.

7. The reactor assembly according to according to claim 1, wherein the reactor has a volume of less than $10^9$ μm$^3$.

8. The reactor assembly according to according to claim 1, wherein the first side and second side comprise at least one membrane, the membranes being located opposite of one another.

9. The reactor assembly according to claim 8, wherein the sides are located at a distance (d) of 0.1-5 μm for a reactor only comprising a liquid or liquids, and at a distance of 0.1-100 μm for a reactor comprising a gas.

10. The reactor assembly according to according to claim 1, wherein the first side and/or second side comprise at least one spacer for maintaining a minimum distance between the first and second side, wherein the at least one spacer is preferably not located under or above the at least one window.

11. The reactor assembly according to claim 9, further comprising at least one second variable capacitor for controlling a distance between the first and second side, and at least one second means for providing an electric field to the at least one second capacitor.

12. The reactor assembly according to according to claim 1, further comprising a controller for controlling a distance between the first and second side.

13. The reactor assembly according to according to claim 1, further comprising at least one heater.

14. Use of a reactor assembly according to claim 1 for one or more of controlling bulging, for fixing a sample, for closing a sub-reaction chamber, for providing pump function, for pre-bending of a first and/or second wall, for applying pressure, for maintaining pressure, for removal or replacement of a gas bubble, for removing unwanted charged particles, for introducing wanted charged particles, and for closing a channel.

15. A microscope comprising a reactor assembly according to claim 1.

* * * * *